United States Patent [19]
Fosang

[11] Patent Number: 5,935,796
[45] Date of Patent: Aug. 10, 1999

[54] DIAGNOSTIC METHODS AND COMPOSITIONS RELATING TO THE PROTEOGLYCAN PROTEINS OF CARTILAGE BREAKDOWN

[75] Inventor: Amanda Jane Fosang, Parkville, Australia

[73] Assignee: The University of Melbourne, Parkville, Australia

[21] Appl. No.: 08/765,061
[22] PCT Filed: Jun. 30, 1995
[86] PCT No.: PCT/AU95/00395
   § 371 Date: Mar. 4, 1997
   § 102(e) Date: Mar. 4, 1997
[87] PCT Pub. No.: WO96/01847
   PCT Pub. Date: Jan. 25, 1996
[51] Int. Cl.$^6$ .............................. G01N 33/53; C12N 5/12; C07K 16/00
[52] U.S. Cl. .................. 435/7.1; 435/7.92; 435/7.93; 435/7.94; 435/326; 530/387.1; 530/387.9; 530/388.1
[58] Field of Search .......................... 435/7.1, 7.9, 7.92, 435/7.93, 7.94, 326; 530/387.1, 387.9, 388.1

[56] References Cited

U.S. PATENT DOCUMENTS 5,108,896  4/1992  Philo et al. ............................... 435/7.5
5,387,504  2/1995  Mumford et al. ........................ 435/7.1

FOREIGN PATENT DOCUMENTS

94/07511  4/1994  WIPO .

OTHER PUBLICATIONS

Nakamura et al, in Handbook of Exp. Immunol, 4th Ed, Weir et al. (eds) Blackwell Scienctific Publications, Chapter 27, pp. 27.3–27.4, 1986.

Doege, et al.; "Complete Coding Sequence and Deduced Primary Structure of the Human Cartilage Large Aggregating Proteoglycan, Aggrecan", pp. 894–902; The Journal of Biological Chemistry, vol. 226, No. 2, (Jan. 15, 1991).

Vilamitjana–Amedee, et al.; "Osteoarthristis–Related Changes in Human Articular Cartilage", pp. 219–227; Arthristis and Rheumatism, vol. 33, No. 2 (Feb. 1990).

Fischer, et al.; "Development of Enzyme Immunoassays Specific for Keratan Sulphate– and Cor–Protein–Epitopes of the Large Aggregating Proteoglycan . . . " pp. 285–291; Eur. J. Clin. Chem. Clin Biochem., vol. 32, No. 4, 1994.

Kahnert, et al.; "Determination of Chondroitin–6–Sulphate by a Competitive Enzyme Immunoassay Using a Biotinylated Antigen", pp. 293–299; Eur. J. Clin. Chem. Clin. Biochem., vol. 32/No. 4 (1994).

*Primary Examiner*—Lila Feisee
*Assistant Examiner*—Susan Ungar
*Attorney, Agent, or Firm*—Larson & Taylor

[57] ABSTRACT

This invention relates to methods and compositions for early diagnosis, monitoring and treatment of cartilage degenerative conditions, including forms of arthritis and are arthropathy, using an antibody which recognizes a peptide comprising the sequence FFGVG . . . generated by cleavage of cartilage aggrecan at the site $N_{341}$-$F_{342}$.

17 Claims, 11 Drawing Sheets

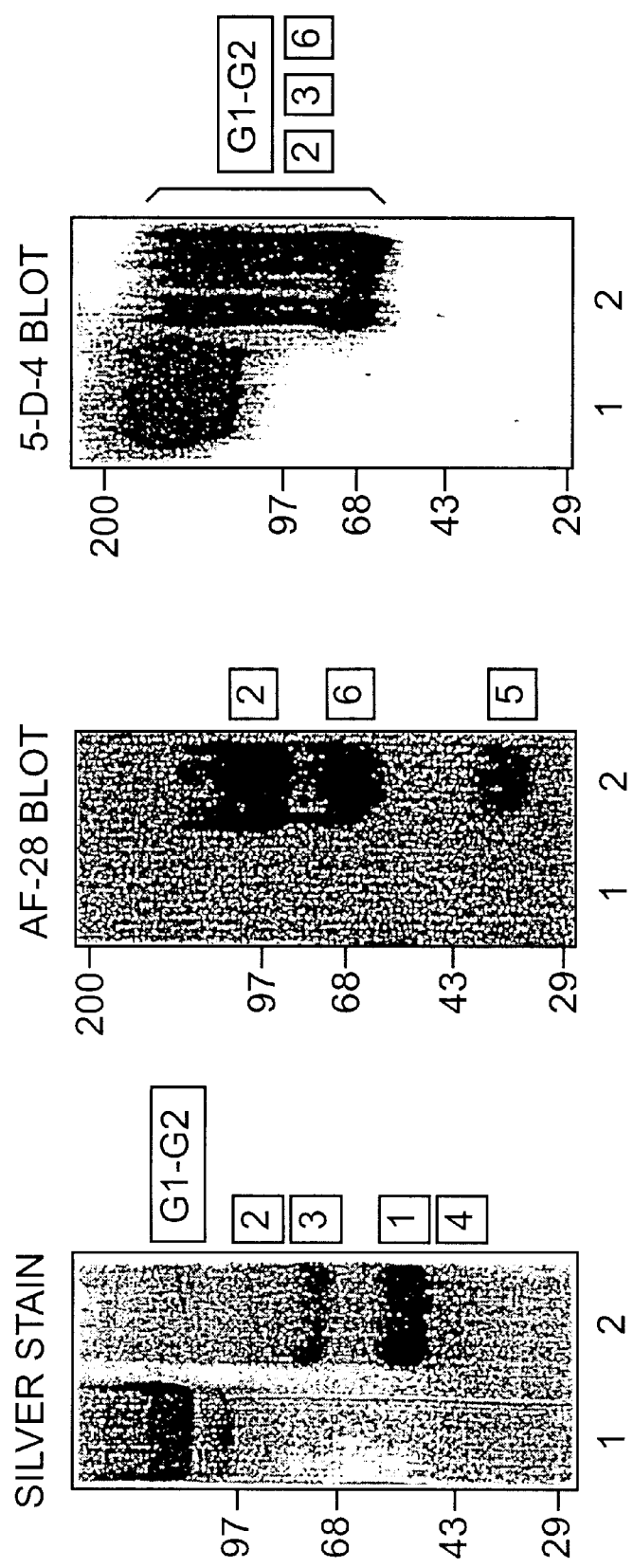

DIAGNOSTIC METHODS AND COMPOSITIONS RELATING TO THE PROTEOGLYCAN PROTEINS OF CARTILAGE BREAKDOWN

FIELD OF THE INVENTION

This invention relates to methods and compositions for early diagnosis, monitoring and treatment of cartilage degenerative conditions, including forms of arthritis. In particular, the invention relates to a peptide generated as a result of enzymic breakdown of a major component of cartilage, and a monoclonal antibody which recognises this peptide.

BACKGROUND OF THE INVENTION

Proteoglycans are widely distributed in the body, and consist of a protein core, to which glycosaminoglycan side chains are covalently linked. The major proteoglycan in cartilage is aggrecan. Collagen and aggrecan are the primary components of the articular cartilage which covers the bones of joints, as well as of other cartilages. Other proteoglycans are also found in skin, tendons, cornea, sclera, intervertebral disc, and elsewhere in the body. They vary in the type and number of the glycosaminoglycan side chains, and in the molecular weight of the protein core. Aggrecan comprises chondroitin sulphate and keratan sulphate side chains.

The proteoglycans, including aggrecan, may be affected in a variety of acute and chronic conditions, including connective tissue diseases such as scleroderma and systemic lupus erythematosus and in degenerative joint conditions, or following trauma. Degenerative joint diseases are frequently referred to as arthritis conditions, and include osteoarthritis, rheumatoid arthritis, psoriatic arthritis, ankylosing spondylitis, and gout, among others.

Arthritis is a crippling musculoskeletal disease that incapacitates millions of people from all walks of life. The two most common forms of arthritis are osteoarthritis (OA) and rheumatoid arthritis (RA). Osteoarthritis alone is the reason for nearly a quarter of all general practitioner consultations. It is present in more than 50% of people over thirty years of age, and statistics released by the Arthritis Foundation of Australia show that one in five Australians is affected. Moreover, the number of people suffering with arthritis is increasing as a consequence of an increasingly elderly population. It is clear that as the incidence of the major killers such as heart disease, cancer and infectious diseases diminishes due to improved public health care, the impact of chronic diseases such as arthritis falls more heavily on the population and on health care systems.

The major feature of both OA and RA is cartilage degradation and loss of aggrecan, the molecule which gives cartilage its unique weight-bearing properties. Most pathological conditions involving proteoglycan destruction are not detected until the disease is relatively advanced. In particular, the initial presenting features of the major arthritides, osteoarthritis and rheumatoid arthritis, are pain, swelling and stiffness. Symptoms do not manifest themselves until the degree of cartilage destruction is already significant.

Very little is known of the precise mechanisms underlying the changes in cartilage that lead to damage, or about what causes the loss of aggrecan and the eventual eburnation of the articular surface. Clearly there is an urgent need for:

(i) a better understanding of the mechanisms involved in aggrecan loss and cartilage destruction, and (ii) the development of better diagnostic techniques for detecting the early stages of joint disease before the damage has become so extensive that tissue repair is no longer possible.

In order to identify the early stages, it is necessary to find a marker of the disease that is regularly observed in cases that are clinically well-defined. There is a particularly urgent need for a reliable method of very early detection of cartilage damage. Such methods are, of course, also applicable to monitoring of disease progression, monitoring of the efficacy of methods of therapy, and screening new therapeutic agents.

Methods of detecting proteoglycan products in biological samples have been proposed for this purpose. Thus, for example, U.S. Pat. No. 4,778,768 by Heinegård and Lindblad and U.S. Pat. No. 5,185,245 by Heimer disclose methods of detecting aggrecan or fragments thereof in synovial fluid, and their use in monitoring changes in articular cartilage and monitoring therapy. U.S. Pat. No. 5,177,020 by Timpl et al discloses the use of immunoassay of heparan sulphate-proteoglycan in body fluids as a method of diagnosis of diabetes mellitus and its complications, such as nephropathy. Australian patent No. 645742 by Caterson and Hardingham discloses the use in diagnostic assays of a monoclonal antibody directed against altered chondroitin sulphate epitopes present in osteoarthritic cartilage. These antibodies detect epitopes present on abnormal chondrotin sulphate/dermatan sulphate chains. However, none of these methods has found wide application, and it appears that they also may be detecting changes which occur relatively late in the development of disease. Early changes must be identified. Therefore, the basic mechanisms involved in initiation of cartilage destruction have been studied intensively by a number of workers. This has required an understanding not only of the detailed structure of the aggrecan molecule, but also identification of the enzymes which can degrade aggrecan, and the sites at which these enzymes cleave the protein core.

Aggrecan is the major proteoglycan in cartilage, and is responsible for its resilience and load-bearing properties. The properties of aggrecan have been extensively studied, and the sequence of the protein moiety is known for several species. The loss of aggrecan is a major feature of the cartilage degeneration associated with arthritis. Normal turnover and pathological loss of aggrecan from cartilage involves proteolytic cleavage of the core protein at the N-terminus, where two globular domains, G1 and G2, are separated by a short interglobular domain (IGD). This is illustrated in FIG. 3 below. The IGD has been identified as a key site of proteolytic attack; however the proteinases responsible for cleavage in the tissue have not been identified, despite intensive study of a variety of candidate enzymes.

The matrix metalloproteinases (MMPs) have long been regarded as the most likely mediators of cartilage destruction. The different kinds of human MMPs are listed in Table 1. The well-documented but circumstantial evidence that implicates the MMPs in aggrecan degradation is as follows:

(i) MMPs-1, -2, -3 and -9 are synthesised by chondrocytes and synovial cells (ii) elevated levels of stromelysin and collagenase have been found in joint fluids of OA and RA patients (iii) synthesis and secretion of MMPs is markedly stimulated both in vivo and in vitro by cytokines such as IL-1 and TNF that are known to promote cartilage resorption.

TABLE 1

The Matrix Metalloproteinases

| | | |
|---|---|---|
| Interstitial collagenase | MMP-1 | EC 3.4.24.7 |
| Neutrophil collagenase | MMP-8 | EC 3.4.24.34 |
| Collagenase-3 | MMP-13 | |
| Gelatinase A | MMP-2 | EC 3.4.24.24 |
| Gelatinase B | MMP-9 | EC 3.4.24.25 |
| Stromelysin-1 | MMP-3 | EC 3.4.24.17 |
| Stromelysin-2 | MMP-10 | EC 3.4.24.22 |
| Stromelysin-3 | MMP-11 | |
| Matrilysin | MMP-7 | EC 3.4.24.23 |
| Metalloelastase | MMP-12 | |
| MT-MMP | MMP-? | |

Our research has focused on the aggrecan IGD, with the aim of determining precisely where enzymes cleave the core protein, and which cartilage enzyme/s are responsible for this cleavage. Using a purified G1-G2 substrate prepared from cartilage aggrecan (1) we have identified cleavage sites specific for all the MMPs except MMP-11, MMP-12, and MT-MMP (2–4, 27), as well as cathepsin B (3) plasmin and urokinase-type plasminogen activator (5). Our results show that all the MMPs cleave at a site located between Asn 341 and Phe 342 (Table 2) (based on the human aggrecan sequence (6)) and that this is the preferred and predominant site of cleavage for this class of enzyme. We have also located a minor MMP cleavage site between Asp 441 and Leu 442; however the incidence of cleavage at this site is low, and not all the MMPs show this activity (3, 4).

However, other studies (7–9) have identified a major cleavage site within aggrecan IGD which was different to the MMP cleavage site, and differed from those characterised for some other candidate proteinases, namely cathepsin B (3), leukocyte elastase (12), plasmin and urokinase (5). These studies have shown that, under conditions of normal and interleukin-1 (IL-1) stimulated turnover, bovine cartilage explants released aggrecan fragments with N-terminal sequences corresponding to cleavage between Glu 373 and Ala 374 (7–9). The amino acid sequences flanking the metalloproteinase and the aggrecanase cleavage sites are given in Table 2.

TABLE 2

Metalloproteinase and aggrecanase cleavage sites in aggrecan IGD

| Proteinase | Cleavage sites |
|---|---|
| Matrix metalloproteinase | ....D I P E N$_{341}$ ↓ F F G V G... |
| Aggrecanase | ...I T E G E$_{373}$ ↓ A R G S V... |

In addition, the major aggrecan fragments found in synovial fluids from OA and joint injury patients result from cleavage at the same Glu 373-Ala 374 bond (10,11). The enzyme responsible for this cleavage has been named aggrecanase, but its identity has remained unknown. With one exception (15,16) all attempts to identify proteinases that can cleave at this aggrecanase site in vitro, or to purify the activity from cartilage or chondrocyte extracts, have failed, despite intense interest from research institutions and the pharmaceutical industry.

It is currently generally accepted in the field that two groups of enzymes are involved in aggrecan breakdown in degenerative joint conditions, namely the matrix metalloproteinase group (Table 1) and the as-yet unidentified but widely accepted "aggrecanase". The cleavage sites for the matrix metalloproteinases and for aggrecanase are different (Asn 341-Phe 342 and Glu 373-Ala 374 respectively), and in most cases the cleavage products are detected by electrophoresis and sequencing.

The identification of aggrecanase-derived fragments in human synovial fluids suggests that "aggrecanase" is the enzyme that is responsible in vivo for loss of aggrecan from cartilage. However, other data indicate that MMPs are also directly involved in aggrecan degradation in vivo: G1 fragments with C-terminal sequences that correspond to MMP cleavage have been extracted from and immunolocalized in human articular cartilage (13,14 respectively). These findings suggest that cleavage by both MMPs and aggrecanase is involved in aggrecan degradation in vivo, and readily explain the occurrence of C-terminal . . . DIPEN fragments in cartilage matrix and N-terminal ARGSV . . . fragments in joint fluids (Table 2).

We have previously reported that a metalloproteinase, MMP-8, can cleave a G1-G2 substrate in vitro at the glu$_{373}$-ala$_{374}$ site, and therefore has aggrecanase activity (15,16). We have also shown that in vitro MMP-8 cleaves primarily at the MMP site, . . . N$_{341}$↓FFGVG . . . , and that cleavage at the aggrecanase site occurs as a secondary event (16). Our data do not imply that MMP-8 is aggrecanase in cartilage, and indeed no MP-8, protein or antigen has been found in cartilage; however, our data do confirm that the metalloproteinases are likely to play a prominent role in aggrecan degradation.

There is one body of thought which considers that the principal event in aggrecan breakdown is cleavage by aggrecanase at Glu 373-Ala 374, and another which considers that cleavage at the MMP site, Asn 341-Phe 342, may be the key event. Collectively, the current available literature would suggest that there is in vivo cleavage at both the MMP and the aggrecanase sites, but it is not known which cleavage is the primary, or rate-determining step.

International patent publication No. WO-93/22429 by Shriners' Hospital for Crippled Children describes the identification of aggrecan fragments in synovial fluid from patients with post-traumatic arthritis caused by recent knee injury, and from patients with early or late stage OA. Biochemical analysis identified a single major N-terminal sequence in all samples, commencing ARGSV . . . . At least two populations of aggrecan fragments, both relatively large and both with the N-terminal sequence ARGSVILXVK . . . were identified. An N-terminal sequence FFGVGGEEDIXVQ . . . was obtained after deglycosylation of chondroitin-sulphate-bearing human aggrecan fragments produced following treatment with stromelysin. These stromelysin fragments showed no evidence of an N-terminal sequence beginning at Ala 374. The inventors proposed a method of monitoring onset or a progression of osteoarthritis comprising assaying biological fluid, such as synovial fluid, for proteoglycan breakdown products, specifically resulting from cleavage of aggrecan between Glu 373 and Ala 374, and in particular where the breakdown product had a N-terminal amino acid sequence ARGSV . . . . While it was suggested that antibody detection was suitable, no specific antibodies were disclosed. It was also proposed that antibodies directed to the aggrecanase cleavage region or enzyme inhibitors comprising the amino acids Glu-Ala could be used for treatment of OA.

At the 40th Annual Meeting of the Orthopaedic Research Society (Feb. 21–24, 1994), monoclonal antibodies were described which are able to detect aggrecan fragments generated by aggrecanase and by metalloproteinase (17–19). monoclonal antibody BC-3 recognises amino-neo-epitope fragment ARGSVIL . . . resulting from digestion of aggrecan by aggrecanase, and antibody BC-4 recognises the carboxy-neo-epitope sequence . . . FVDIPEN resulting from digestion of aggrecan with the metalloproteinase stromelysin (17). Monoclonal antibody BC-3 detects aggrecan peptides with N-terminal sequence ARGSV . . . , which is produced in vivo by the action of aggrecanase, and also in vitro by neutrophil collagenase (matrix metalloproteinase-8; MMP-8) (15,16). A polyclonal antibody recognising the peptide FVDIPEN (SEQ ID NO. 1) detected fragments resulting from the action of stromelysin or gelatinase A (18–19, 28); the antibody requires the sequence VDIPEN (SEQ ID NO. 2) for full recognition of the peptide. This antibody was able to detect aggrecan fragments in synovial fluid (19) and in cartilage (14,19).

There have so far been no reports of any antibody against the carboxy-neo-epitope with N-terminal sequence FFGVG . . . resulting from matrix metalloproteinase action, or that such an antibody could in fact detect aggrecan fragments in biological samples.

The amino acid sequences flanking the metalloproteinase site and the aggrecanase site in the IGD are shown in Table 2 above. The newly-created N- and C-termini generated by proteolysis at these sites represent neo-epitopes with antigenic determinants that are different to the antigenic determinants present on sequences in the intact, undegraded protein. Potentially, neo-epitope antibodies are enormously useful for detecting discrete products of aggrecan degradation. Importantly, in OA cartilage specimens, the . . . DIPEN epitope was specifically immunolocalised in regions exhibiting extensive fibrillation and loss of aggrecan (14), providing in vivo evidence for metalloproteinase involvement in joint disease.

To investigate MMP action further we have developed a novel neo-epitope monoclonal antibody. We have produced a mono-specific hybridoma that secretes IgG$_1$ specific for the N-terminal FFGVG . . . sequence generated by MMPs. This antibody is diagnostically more useful than the anti-DIPEN antibody, because it detects the FFGVG . . . epitope that is released from the tissue into the synovial space, whereas the . . . DIPEN epitope located on the G1 domain is predominantly retained in the tissue.

SUMMARY OF THE INVENTION

In a first aspect, the invention provides an antibody which recognises a peptide comprising the sequence FGVG . . . (phenylalanine-phenylalanine-glycine-valine-glycine), representing the N-terminal sequence of the carboxy-terminal product generated by cleavage of aggrecan at the site N341-F342. Preferably the antibody is a monoclonal antibody. More preferably, the antibody is monoclonal antibody AF-28, as described herein.

According to a second aspect, the invention provides a method of detecting an aggrecan degradation product in a sample, comprising the step of reacting said sample with an antibody which recognises the N-terminal sequence FFGVG . . . . The sample may be a mammalian body fluid, and is preferably blood, serum, synovial fluid, lymph or urine. More preferably the body fluid is of human origin. Alternatively, the biological sample may be a cell or tissue culture medium. The person skilled in the field will recognise that for certain applications other biological samples may be suitable. Such a person will also recognise that the antibody may give stronger binding to a longer N-terminal sequence of the aggrecan fragment.

In a preferred embodiment, the method is a competition ELISA assay in which the competing peptide is FFGVGG (SEQ ID NO. 3); more preferably the competing peptide is FFGVGGEEDITVQTVTWPDMELPLPRNITEGE (FFGVG . . . EGE 32-mer) (SEQ ID NO. 4), as herein described.

In a more preferred embodiment, the method is a sandwich ELISA which improves the sensitivity of detection of epitopes in serum. Such an assay may suitably involve coating ELISA plates with an anti-keratan sulphate antibody, such as 5-D-4, or an anti-aggrecan antibody and using this as a "capture" antibody to bind aggrecan fragments. Those aggrecan fragments containing the FFGVG . . . epitope can then be detected with labelled AF-28 antibody. For example, AF-28 can be labelled either with biotin or horseradish peroxidase (HRP), and detected with the HRP substrate ABTS or luminol. Alternatively Dynabeads (Trademark), magnetic polystyrene beads, can be coated with 5-D-4 and used to bind aggrecan fragments, followed by AF-28 in the same way. The Dynabead technique employs magnetic separations. The person skilled in the art will be aware of a variety of other labelling and detection methods.

In a third aspect, the invention provides a method of diagnosis of a condition involving aggrecan breakdown in a mammalian subject, comprising the step of subjecting a biological sample from said subject to a test for detection of an aggrecan breakdown product, using an antibody of the invention.

In a fourth aspect, the invention provides a method of monitoring progress of a condition involving aggrecan breakdown in a mammalian subject or of monitoring efficacy of treatment of such a condition, comprising the step of periodical testing of a biological sample from said subject for the presence of an aggrecan breakdown product, using the antibody of the invention.

In both the third and fourth aspects of the invention, preferably the subject is human, and preferably the condition involving aggrecan breakdown is a degenerative joint disease or is joint trauma. Preferably the degenerative joint disease is any form of arthritis or arthropathy, more preferably selected from the group consisting of rheumatoid arthritis, juvenile chronic arthritis (JCA), osteoarthritis (OA), psoriatic arthritis, haemophilic arthritis, suppurative arthritis, gout and Crohn's arthropathy.

According to a fifth aspect, the invention provides a method of screening of putative therapeutic agents for the prevention of aggrecan breakdown, comprising testing the ability of the putative agents to inhibit aggrecan breakdown, and comprising the step of detecting aggrecan breakdown products using the antibody of the invention. Suitable model systems for use in such screening methods include in vitro digestion using whole aggrecan, purified aggrecan G1-G2 as substrate, or cartilage explant cultures treated with inducing agents such as retinoic acid or interleukin-1.

The invention also includes within its scope therapeutic agents identified using this method of screening. It is contemplated that these agents will include antibodies, particularly monoclonal antibodies, or antigen-binding fragments thereof, which are specific for the MMP cleavage site of aggrecan, or for the region of the aggrecan molecule which comprises this cleavage site. Such antibodies are able to bind to the aggrecan molecule so as to prevent access of MMP to the cleavage site. Alternatively, antibodies which bind to the MMP, particularly to the active site thereof, are suitable; such antibodies reduce or abolish the activity of the MMP by binding to the enzyme, so as to prevent it from binding to the cleavage site in the aggrecan molecule. Alternatively, inhibitors of MMP activity may be used. These, for example, may be peptides of relatively low molecular weight, and preferably comprise the Asn-Phe cleavage site. Such peptides act as competitive inhibitors of the MMP enzyme. Other inhibitors of MMP activity are known, for example peptidylhydroxamate compounds such as the leucylphenylalaninamide derivative U24522 (20,21).

It will be appreciated by the person skilled in the art that any convenient system may be used for detection of aggrecan breakdown products using the antibody of the invention. For example, enzyme-linked immunosorbent assays (ELISA assays), radioimmoassays, fluorescence immunoassays, chemiluminescent assays, immunoprecipitation assays, immunohistochemical assays, Western blot analysis, and dot-blot analysis are all contemplated to be suitable for use in the methods of the invention. The most convenient methods for diagnostic purposes or for purposes of monitoring progress of disease or efficacy of treatment are likely to be ELISA, fluorescence immunoassay, chemiluminescent immunoassay, or radioimmnoassay. Western blot analysis using enhanced chemiluminescent detection permits detection of epitopes which are present at very low concentrations.

A suitable standard for use in the immunoassays of the invention is recombinant aggrecan interglobular domain (IGD). Such recombinant IGD may be produced by methods known in the art, such as expression of recombinant non-glycosylated IGD as a fusion protein with glutathione-S-transferase in *Escherichia coli* using the commercially-available pGEX-2T expression vector (22). Other methods, including expression in insect cells using the baculovirus system, and other expression systems and expression vectors, are known to those skilled in the art. Alternatively, highly purified MMP-treated aggrecan core protein, or synthetic peptides, may be used as standard.

BRIEF DESCRIPTION OF THE DRAWINGS

The invention will now be described in detail by way of reference only to the following non-limiting examples, and to the figures, in which:

FIG. 1A shows silver staining, FIG. 1B shows immunodetection with AF-28.

FIG. 5A–5C shows the results of Western blot analysis of fragments generated from digestion of purified aggrecan G1-G2 by MMP-8 for 21 hours, followed by digestion with keratanase. Aliquots of undigested G1-G2 (lane 1) and digested G1-G2 (lane 2) were detected by FIG. 5A silver stain, FIG. 5B monoclonal antibody AF-28 and FIG. 5C monoclonal antibody 5-D-4.

FIG. 9A shows samples from patients with inflammatory arthritis and rheumatoid arthritis;

FIG. 9B shows results obtained using extended electrophoresis times. Synovial fluids from the same patients as in FIG. 9A are compared with synovial fluids from JCA and OA patients.

DETAILED DESCRIPTION OF THE PREFERRED EMBODIMENT

The invention is described in connection the following examples and with reference to the figures.

EXAMPLE 1

Monoclonal Antibody Specific for the N-Terminal Sequence FFGVG . . . Specifically Detects Aggrecan Fragments Produced by Digestion with Matrix Metalloproteinases A synthetic peptide FFGVGGEEDC (SEQ ID NO. 8), prepared by conventional solid-phase methods, was coupled to keyhole limpet haemocyanin (KLH) carrier protein using the heterobifunctional agent 6-maleimido-caproic acid N-hydroxysuccinimide ester to form a peptide conjugate. Monoclonal antibodies were produced using standard procedures. Balb/c mice were immmunized with 75 μg of the conjugate emulsified in Freund's complete adjuvant and boosted with an equivalent dose 7 weeks later. Spleen cells from these mice were fused with SP₂O cells and hybrid cells were isolated using the 'HAT' selection procedure [29]. Hybridomas were screened against KLH and FFGVGGEEDC-KLH antigens coated on ELISA plates. Antibody in the culture fluids which bound to antigen was detected with anti-mouse horse-radish peroxidase (HRP) conjugates, using colour development with ABTS substrate. Clones positive against KLH alone were discarded, and clones positive against peptide conjugated to KLH were recloned by limiting dilution. One of the resulting hybridoma cell lines, which was positive for peptide reactivity, was designated AF-28, and was expanded in culture and maintained as ascites cells in mice using conventional methods. A sample of the hybridoma cell line AF-28 was deposited in the American Type Culture Collection, 12801 Parklaron Drive Rockville, Md. 20852, USA pursuant to the provisions of the Budapest Treaty on Jul. 6, 1994 under the accession number ATCC HB 11671. The hybridoma antibody was identified as being subclass $IgG_1$ by ELISA isotyping.

Ascitic fluid containing the monoclonal antibody was tested for immunoreactivity against a number of antigens by Western blot analysis and by enzyme-linked immunosorbent assay. To meet our requirements it was essential that the antibody recognise only the N-terminal sequence of the immunising peptide FFGVGGEEDC (SEQ ID No. 8), and not an internal sequence. Thus, the antibody should detect only aggrecan fragments containing the FFGVG . . . N-terminal sequence produced by digestion with matrix metalloproteinases, and not undigested aggrecan, nor aggrecan digested with enzymes that cleave at sites which are different to the major MMP site.

Figure 1A:
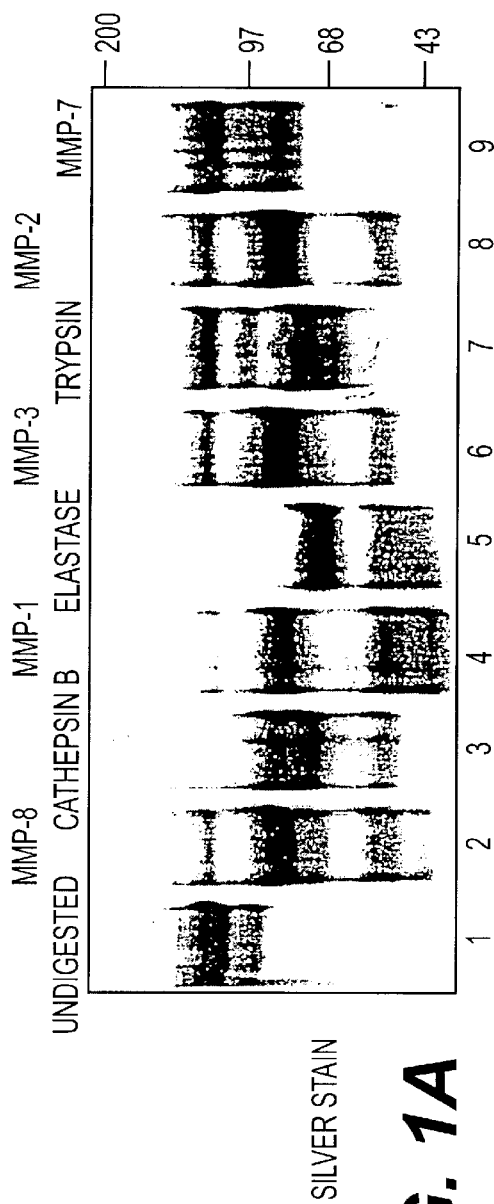
FIGS. 1A and 1B show detection of aggrecan cleavage fragments using monoclonal antibody AF-28. Purified aggrecan G1-G2 (5 μg) was digested with 125 μg/ml purified human MMP-8 (lane 2), 100 μg/ml recombinant rat cathepsin B (lane 3), 117 μg/ml recombinant human WP-1 (lane 4), 0.1 units/ml purified elastase (lane 5), 10 μg/ml recombinant human stromelysin (lane 6), 1 μg/ml trypsin (lane 7), 10 μg/ml purified human MMP-2 (lane 8), or 5.2 μg/ml recombinant human matrilysin (lane 9). Lane 1 shows undigested G1-G2. Following digestion with proteinases, the samples were treated with keratanase I prior to electrophoresis.
Figure 1B:
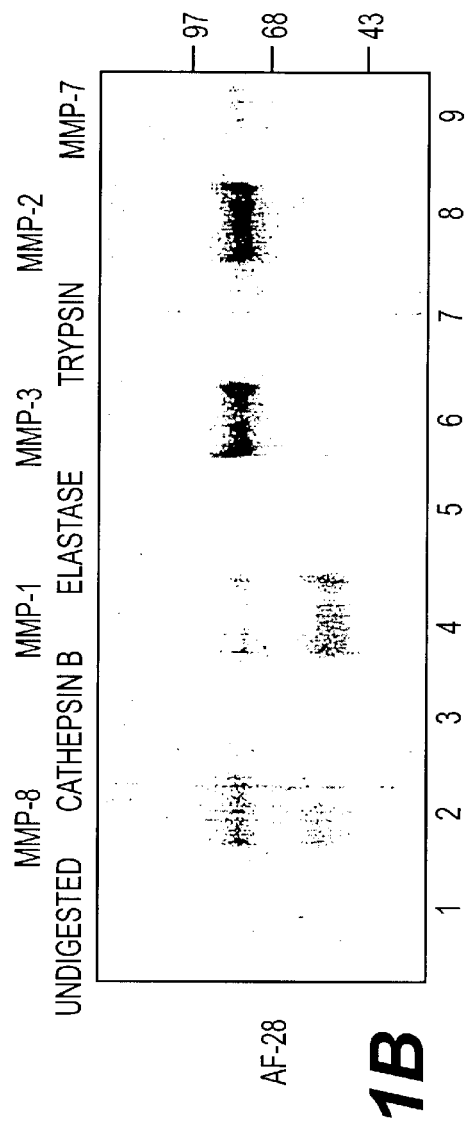

A G1-G2 fragment isolated from pig laryngeal aggrecan (1) was digested with MMP-1, MMP-2, MOP-3, MMP-7, and MMP-8. The major activity of these MMPs is cleavage at DIPEN↓FFGVG (2–4). G1-G2 was also digested with cathepsin B, elastase and trypsin, which do not cleave at the major MMP site (3, 12). Aliquots of digested and undigested G1-G2 were electrophoresed in duplicate on 5% SDS gels (23) for detection by silver stain (FIG. 1A) or transfer to polyvinylidene difluoride membranes. (Immobilon; Millipore-Waters) and immunodetection with AF-28 (FIG. 1B). The results show that AF-28 specifically detects products of MMP digestion, but not undigested G1-G2 or fragments produced by cathepsin B, elastase or trypsin digestion. A single AF-28 positive band, of $M_r$ 85 kDa, was found in the MMP-3, MMP-2 and MMP-7 digests, and this corresponds with the 85 kDa G2 band which has been isolated and sequenced previously (2-4). MMP-1 and MMP-8 produced two AF-28 positive bands, consistent with these enzymes cleaving G1-G2 at the major MMP site, as well as a second site in the IGD (4) (see also FIG. 4).

EXAMPLE 2

Figure 2A:
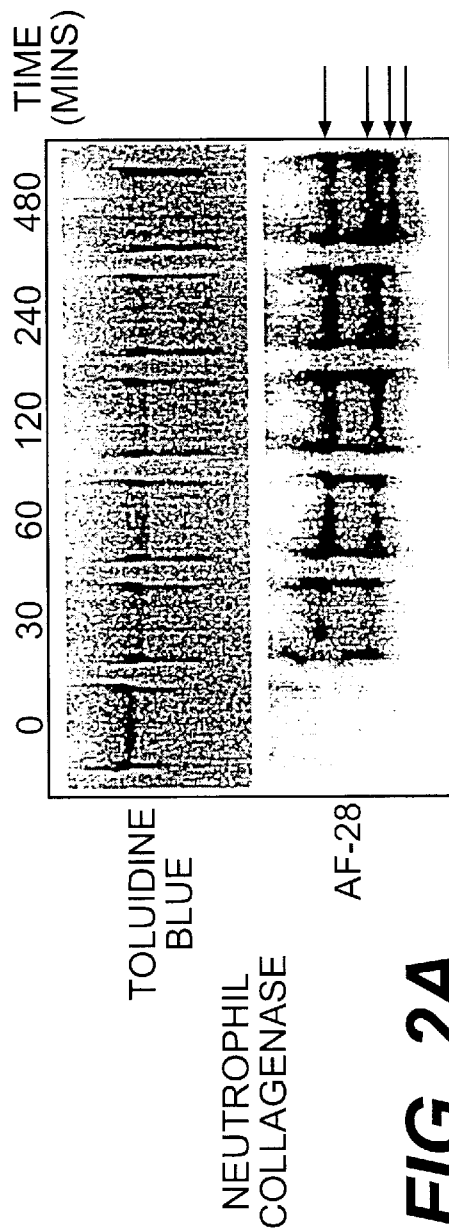
FIGS. 2A and 2B show results of an experiment in which purified aggrecan was digested with 140 μg/ml purified human MMP-8, FIG. 2A, or recombinant human MMP-1, FIG. 2B, for 30, 60, 120, 240 or 480 minutes. The first track shows undigested aggrecan.
Figure 2B:
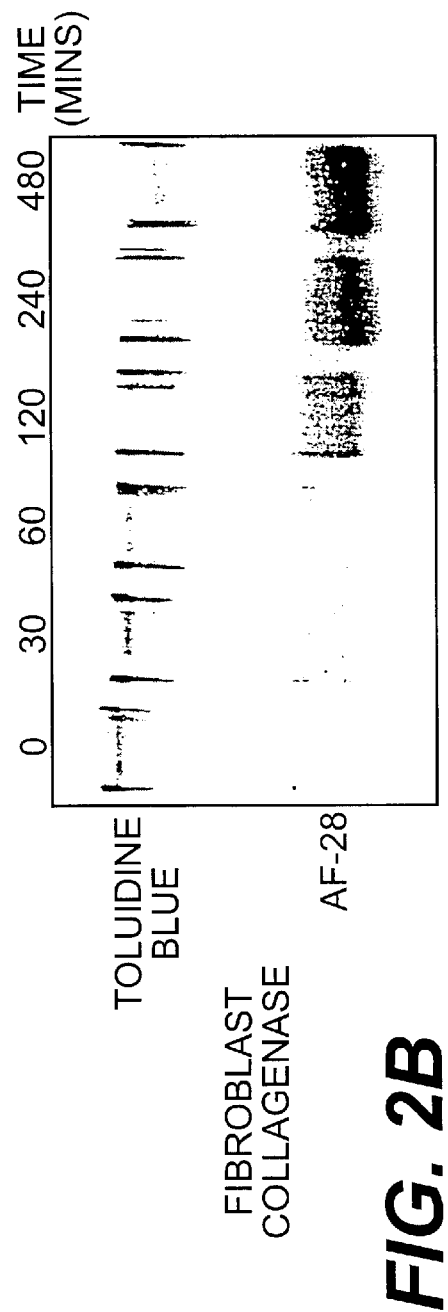

Monoclonal Antibody A-28 Recognises Fragments Produced by Digestion of Whole Aggrecan Whole aggrecan purified from pig laryngeal cartilage was digested with either MMP-8 (neutrophil collagenase) (FIG. 2A) or MMP-1 (fibroblast collagenase) (FIG. 2B) for 30, 60, 120, 240 or 480 minutes. Aliquots of digested and undigested aggrecan were electrophoresed in duplicate on agarose/polyacrylamide composite gels (24) for detection with toluidine blue or transfer to immobilon membranes for immunodetection with AF-28. The results show that undigested aggrecan was not detected by AF-28, but AF-28 positive bands could be detected at all subsequent times of digestion. MMP-8 produced three major and one minor AF-28 positive fragments after 4 hours digestion (FIG. 2A, arrows); however MMP-1 produced a single major AF-28 positive band after the same digestion time (FIG. 26).

The results of Examples 1 and 2 confirm the neo-epitope nature of the epitope recognised by AF-28.

EXAMPLE 3

Monoclonal Antibody AF-28 Identifies Predicted Digestion Products of Aggrecan G1-G2

Figure 3A:
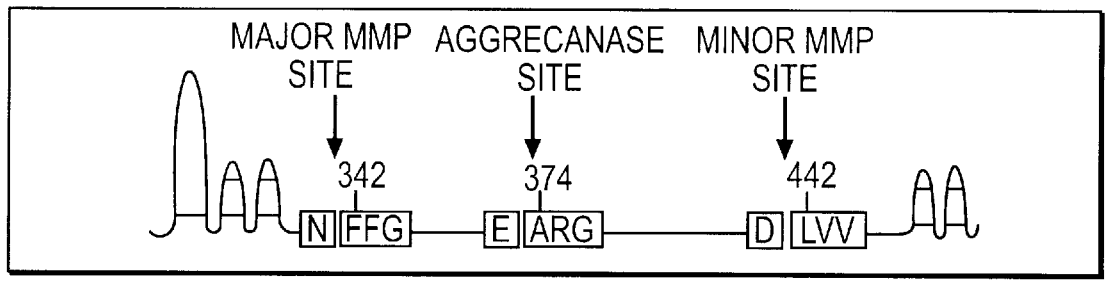
FIGS. 3A and 3B are schematic representations of the aggrecan G1-G2 fragment, showing the three known MMP-8 cleavage sites and the seven predicted products resulting from cleavage at these sites.
Figure 3B:
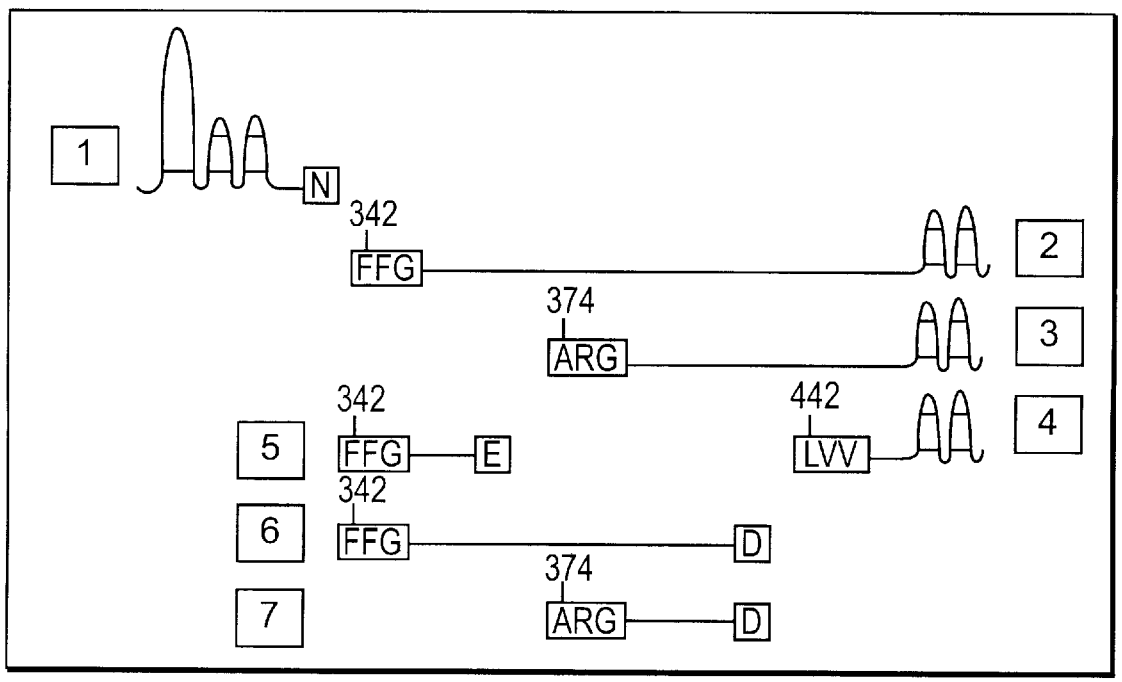

We have previously reported that MMP-8 can cleave G1-G2 not only at the major and minor MMP sites, but also at the aggrecanase site (15,16). These studies suggested that G1-G2 digested with MMP-8 should produce seven different fragments, and that three of these fragments would have FFGVG . . . N-terminal sequences (FIG. 3A and 3B). Of the seven fragments, four contained globular G1 or G2 domains (FIGA. 3A and 3B, fragments 1–4), and these fragments were readily detected by silver stain, as shown in Example 1. Three other fragments lacking globular domains (FIG. 3A and 3B, fragments 5–7) were predicted to be derived from the IGD, but were not detected by silver stain. Two of these fragments were predicted to have FFGVG . . . N-terminal sequences, (FIGS. 3A and 3B, fragments 5 & 6).

Figure 4:
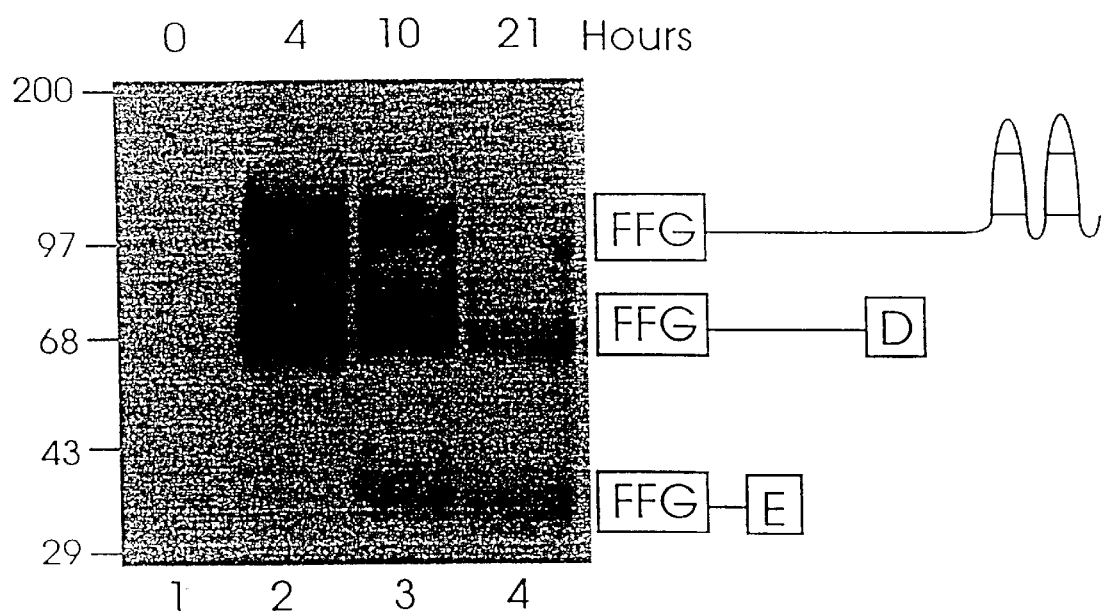
FIG. 4 shows the results of Western blot analysis of fragments generated from digestion of purified aggrecan G1-G2 by MMP-8 for 4, 10 or 21 hours, followed by digestion with keratanase. Aliquots of the undigested G1-G2 (lane 1) and digested G1-G2 (lanes 2–4) were detected using AF-28 monoclonal antibody.

G1-G2 was digested with 160 $\mu$g/m MMP-8 for 4, 10 or 21 hours. The samples were then digested with keratanase prior to electrophoresis and transfer to immobilon for immunodetection with AF-28 by Western blot analysis (FIG. 4). The results presented in FIG. 4 show that three AF-28 positive bands, corresponding to the predicted fragments, could be detected; of these, the two smallest bands (30 and 60 kDa) have not been detected previously.

Cleavage by MMP-8 at the identified sites would produce three fragments with FFGVG . . . N-terminal sequences as shown in FIGS. 3A and 3B, and following Western analysis, three bands were detected with AF-28 antibody (FIG. 5B, lane 2). The largest fragment detected with AF-28 corresponds in size to fragment 2, which we have characterised and shown to have an FFGVG . . . N-terminus (16). The silver-stained gel showed the products previously identified (16). However, the two faster migrating fragments identified with AF-28 (about 30 and 60 kDa) were not readily detected on the silver stained gel (FIG. 5A, lane 2). As there are only three cleavage sites and fragments 1–4 have previously been identified by sequencing and immunodetection, it is therefore most likely that these two smallest fragments detected by AF-28 antibody correspond to fragments 5 and 6. Because these fragments are glycosylated non-globular protein sequences they would not be expected to stain well with silver, and this would explain our failure to detect them in previous experiments.

Keratan sulphate chains present on G1-G2 were immunodetected with monoclonal antibody 5-D-4, which recognises a highly sulphated five disaccharide unit of keratan sulphate (25). This monoclonal antibody is commercially available from ICN Biomedicals (Australasia) Pty Ltd. The 5-D-4 epitope is resistant to keratanase digestion, but can be completely removed by keratanase II digestion. The 5-D-4 antibody detected undigested G1-G2 and a range of digestion products from about 60–150 kDa that were poorly resolved from each other (FIG. 5C). The G1 domain and fragment 5 were not detected with 5-D-4 in this experiment.

EXAMPLE 4

Competitive ELISA Assay for the FFGVG Epitope

Figure 6A:
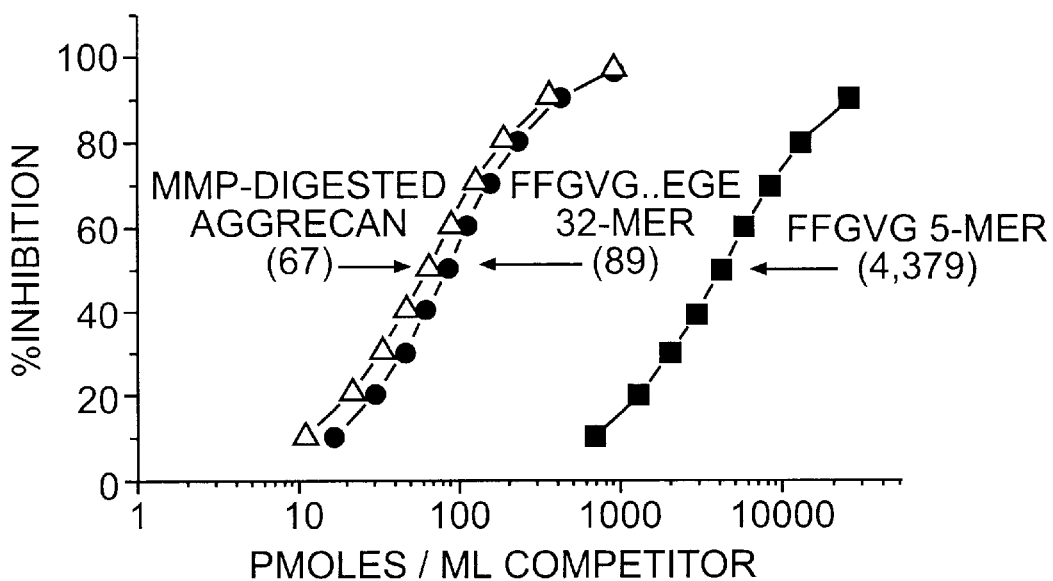
FIGS. 6A and 6B show the results of two competition ELISA experiments for the FFGVG . . . epitope. ELISA plates were coated with either 125 pmoles/ml 32-mer (FIG. 6A) or 25 pmoles/ml 32-mer (FIG. 6B) and the following competitors were tested: FFGVG . . . EGE 32-mer (SEQ ID NO. 4), FFGVG 5-mer (SEQ ID NO. 5), FGVGGEEDI 9-mer (SEQ ID NO. 6) and MMP-digested aggrecan. Undigested aggrecan and DIPENFFGVG 10-mer (SEQ ID NO. 7) were also tested as negative controls.
Figure 6B:
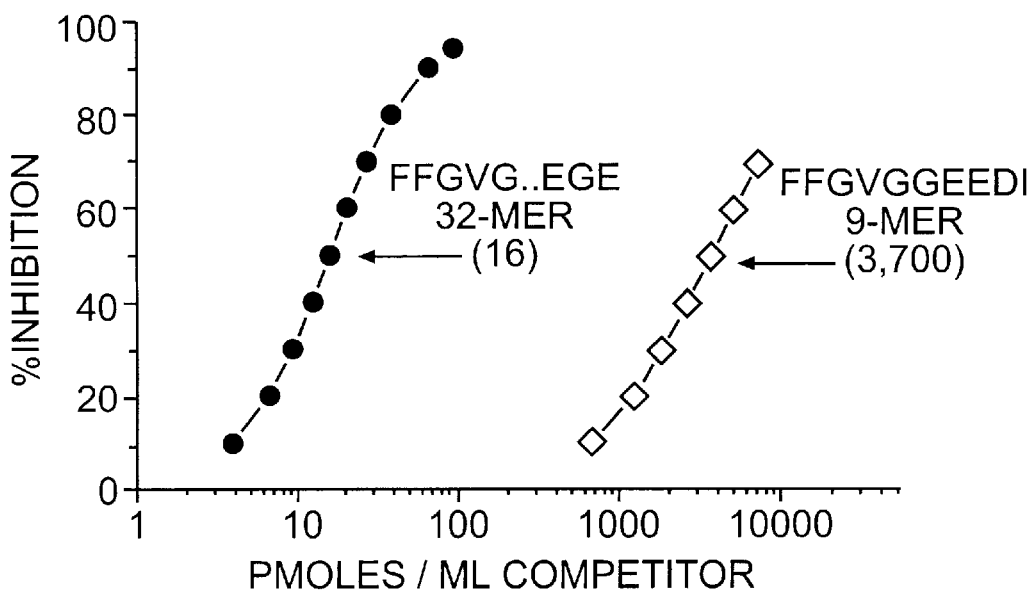

An enzyme-linked immunosorbent assay was devised for the purpose of measuring AF-28 epitope in biological fluids from arthritic patients, and in samples from experimental systems, including animal models. Ninety-six well ELISA plates were coated with a 32-mer synthetic peptide with sequence $F^{342}FGVGG$ . . . $EGE^{373}$ (SEQ ID NO. 4), i.e.

identical with the sequence in the human aggrecan IGD (6), at either 125 pmoles/ml (FIG. 6A) or 25 pmoles/ml (FIG. 6B). Competition experiments were performed using (i) FFGVG (SEQ ID NO. 5) 5-mer, (ii) DIPENFFGVG (SEQ ID NO. 7) 10-mer, (iii) FFGVG . . . EGE (SEQ ID NO. 4) 32-mer, (iv) FGVGGEEDI (SEQ ID NO. 6) 9-mer, (v) undigested pig aggrecan and (vi) MMP-digested pig aggrecan as competitors. Aggrecan was digested with 140 μg/ml MP-8. This concentration of MMP-8 completely degraded GI-G2 substrate, as determined by SDS-PAGE. Binding of AF-28 to the plate was detected with anti-mouse immunoglobulin conjugated to horse-radish peroxidase, and colour development was measured at 405 nm after addition of the peroxidase substrate ABTS. Representative results are shown in FIGS. 6A and 6B. The 50% inhibition values for each competitor are given in parenthesis. No data points are shown for undigested aggrecan and DIPENFFGVG (SEQ ID NO. 7), which were uncompetitive in the assay.

Competitors lacking FFGVG N-terminal sequences (DIPENFFGVG (SEQ ID NO. 7) and undigested aggrecan) gave no competition in the assay, and maximum antibody binding to the plate was observed at all concentrations of these competitors. The MMP digested aggrecan and the 32-mer synthetic peptide were equally competitive in the assay on a molar basis, indicating that the 32-mer was a suitable coating antigen and standard competitor for assaying AF-28 epitope. These results also suggest that keratan sulphate sub st itution in the IGD does not interfere with the detection of AF-28 epitope, since substituted antigen (aggrecan) and unsubstituted antigen (32-mer) were equally competitive on a molar basis. The FFGVG 5-mer (SEQ ID No. 5) was approximately 50 times less competitive than the 32-mer, while the FGVGGEEDI 9-mer (SEQ ID NO. 6) which lacked the N-terminal phenylalanine residue, was approximately 230 times less competitive. These results confirm that AF-28 is a true neo-epitope antibody.

Undigested substrates with internal . . . FFGVG . . . sequences fail to compete in competition assays. In contrast, weak competition can be obtained at high concentrations of peptides containing partial or truncated versions of the epitope (FFGVG 5-mer (SEQ ID NO. 5) and FGVGGEEDI 9-mer (SEQ ID NO. 6)), provided they are present as N-terminal sequences.

Using the 32 mer as both coating and standard antigen, the assay was linear over the range 5–50 pmoles/ml and the 50% inhibition value was approximately 16 pmoles/ml (FIG. 6B).

EXAMPLE 5

Detection of the FFGVG . . . Epitope in A2/A3 Fractions of Cartilage Extracts

Figure 7:
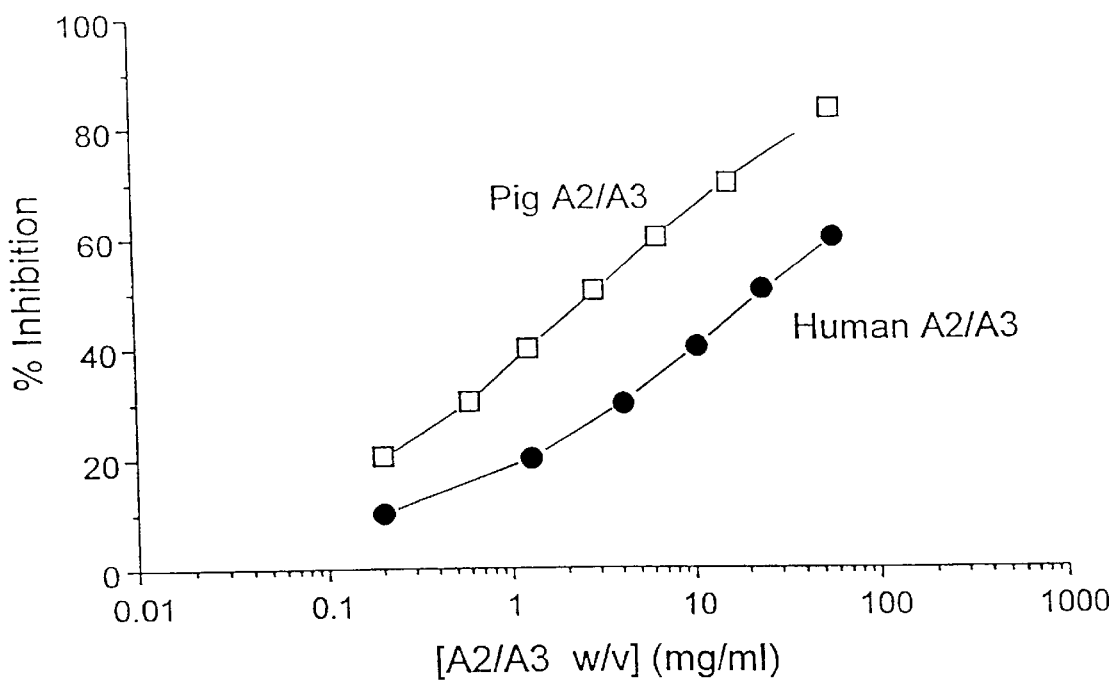
FIG. 7 shows the results of competition experiments with aggrecan fragments extracted from human and porcine cartilage and isolated by CsCl density gradient fractionation.

Guanidine extracts of pig laryngeal cartilage and human articular cartilage (43 year old male without joint disease) were fractionated on associative caesium chloride (CsCl) density gradients to separate aggrecan from other cartilage proteins. Large aggrecan fragments were recovered in the bottom third of the gradient (designated the A1 fraction), while other cartilage proteins and small aggrecan fragments were recovered in the top two-thirds of the gradient (A2/A3 fraction). Guanidine (4M) ext racts of human articular or pig laryngeal cartilage were fractionated on CsCl density gradients, and AF-28 epitope present in the low density fractions (A2/A3) was demonstrated by competition in the assay described in Example 6 below. We assayed the A2/A3 fraction of pig and human cartilage extracts to determine whether any small aggrecan fragments with AF-28 N-terminal epitope were retained in the tissue (FIG. 7). Pooled A2/A3 fractions which had been freeze-dried were reconstituted to 20 mg/ml (w/v) in water and doubling dilutions were tested for their competitiveness in the assay. The results show that low levels of AF-28 epitope, derived from metalloproteinase cleavage of aggrecan, could be detected in these samples, and suggest that while the majority of aggrecan fragments are quickly lost from the tissue into the joint space, a proportion of fragments are either trapped, or specifically retained within the tissue.

EXAMPLE 6

Detection of the FFGVG . . . Epitope in Synovial Fluid of Arthritic Patients

Paired samples of knee joint synovial fluid, blood and urine were collected from arthritic patients attending the Rheumatology Clinics at the Royal Melbourne Hospital and the Royal Children's Hospital. Synovial fluids were obtained from the knee joints of patients requiring either diagnostic or therapeutic aspiration. Complete aspirations of joint fluid were performed under aseptic conditions, without anaesthetic, using a 1.2 mm bore needle, and the total fluid volumes measured. The fluids were collected into sterile tubes, centrifuged within 1 hour to remove cells and stored frozen at −20° C. Blood samples (up to 10 ml) were collected into sterile tubes and allowed to clot for 2 hours at room temperature, then centrifuged and the serum stored at −20° C. Urine specimens were stored frozen. Prior to analysis, samples were desalted and concentrated by ultrafiltration through Millipore filters with 1,000 MW cut-off.

Figure 8:
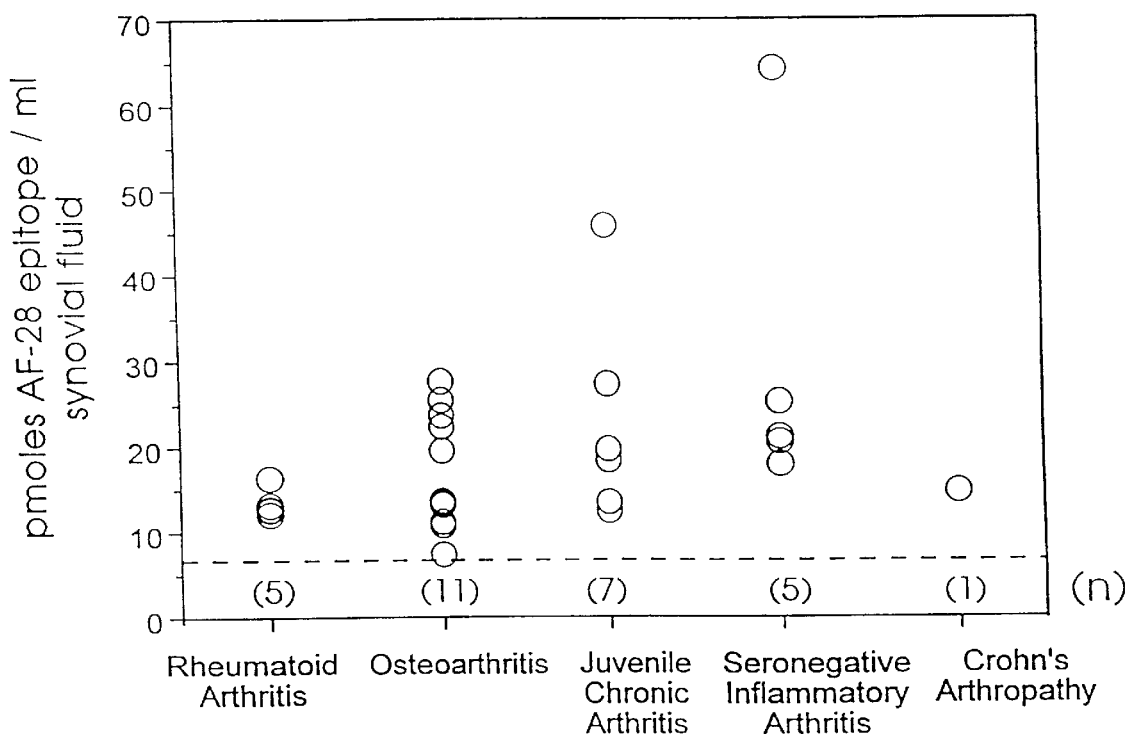
FIG. 8 shows the AF-28 epitope levels in synovial fluid collected from patients with rheumatoid arthritis, osteoarthritis, JCA, seronegative inflammatory arthritis and Crohn's arthropathy.

Aggrecan fragments released from cartilage are present in synovial fluids and serum, and numerous studies have measured protein and carbohydrate epitopes on these fragments. We tested aliquots of hyaluronidase-treated human synovial fluids for the presence of AF-28 epitope by competition ELISA. Synovial fluids were collected from patients with rheumatoid arthritis (n=5), osteoarthritis (n=11), juvenile chronic arthritis (n=7), seronegative inflammatory arthritis (n=5), and Crohn's arthropathy (n=1). Of thirty-three synovial fluid samples tested, twenty-nine contained detectable levels of AF-28 epitope (range 12.4 to 58.2 pmoles/ml with mean 20.6±10.8 pmoles/ml). These results are shown in FIG. 8.

Overnight digestion of synovial fluid samples with chondroitinase ABC, keratanase, keratanase II or 10 μg/ml trypsin did not increase or diminish the level of AF-28 epitope detected in the ELISA, indicating that substituted glycosaminoglycans do not interfere with detection, and that trypsin fragments remain large enough to be fully competitive in the assay.

Figures 9A, 9B:
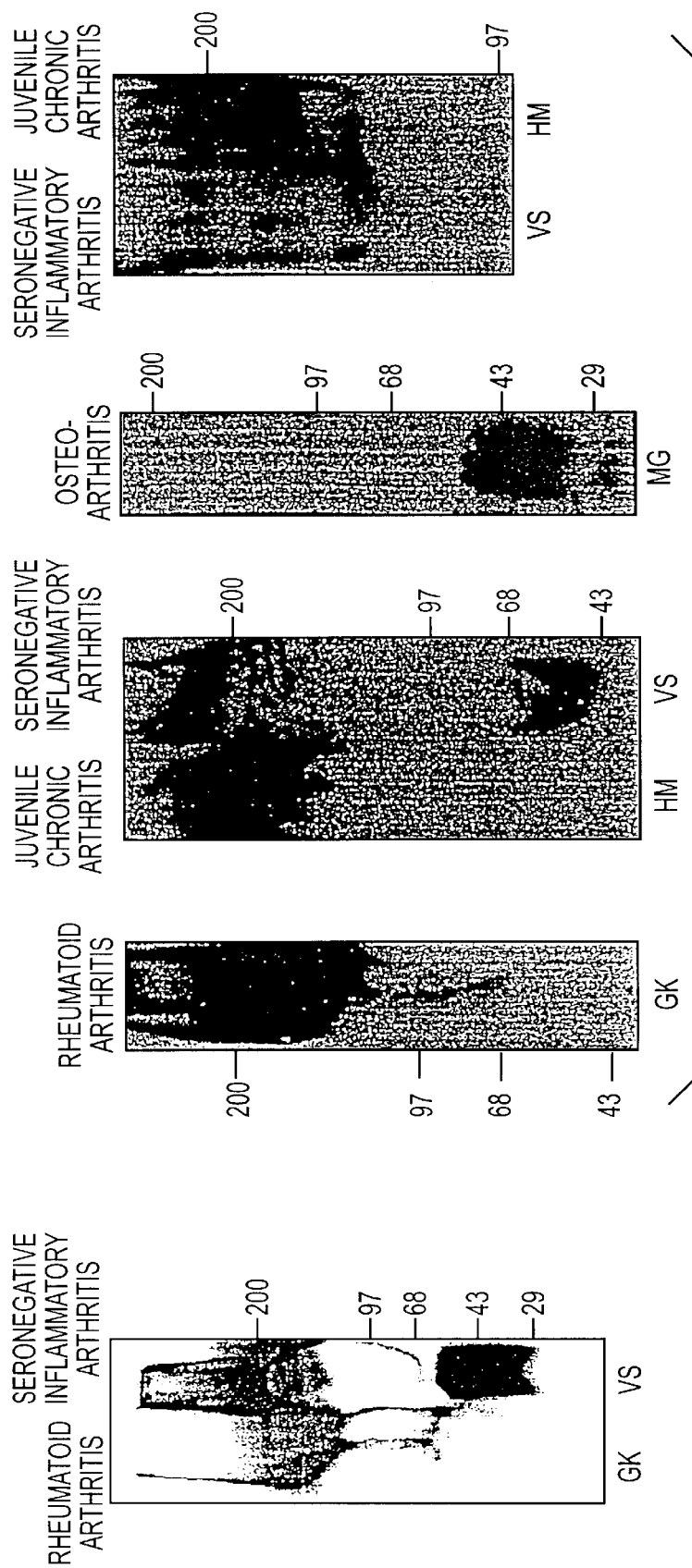
FIGS. 9A and 9B show the results of Western blot analysis of synovial fluids.

In a preliminary experiment, two synovial fluid samples were analysed for the presence of AF-28 epitope by Western analysis, following hyaluronidase digestion to reduce the viscosity of each fluid (FIG. 9A). Even after hyaluronidase treatment large molecular weight polymers were present in the samples. These enter the gel slowly, resolve poorly and cause distortions near the top of the gel. Some staining which may be specific or non-specific is associated with this smear around the 200 kDa marker. However, the major finding was the presence of a broad band with molecular size between 35–55 kDa. This band gave a strong signal in a patient with seronegative inflammatory arthritis. we predict that this band represents the product of proteinase cleavage at both the aggrecanase site and the metalloproteinase site, which yields the 32 amino acid IGD fragment, $F_{342}FGVGG$ ... $EGE_{373}$ (SEQ ID NO. 4)that we have identified in pig G1-G2 digests (FIGS. 3A–3B to 5A–5C). In a second experiment, aliquots of human synovial fluids were electrophoresed on 5% SDS gels and tested by Western blot analysis for AF-28 epitope (FIG. 9B). AF-28-positive material was present in broad, ill-defined bands in the molecular weight range 150–250 kDa (FIG. 9B). These high molecular weight fragments migrated poorly on 5% gels despite hyaluronidase treatment to reduce the viscosity of the fluids. However, if the electrophoresis was continued until the 68 kDa protein standard ran off the bottom of the gel, the broad smear resolved into three discrete bands (FIG. 9b). Again, synovial fluids from two patients, one with sero-negative inflammatory arthritis (FIGS. 9A and 9B, patient VS) and the other with osteoarthritis (FIG. 9B, patient MG), produced a striking broad band on 5% gels with approximate Mr 40–60,000 that reacted strongly with AF-28 antibody. As reaction with the antibody shows it to have the correct FFGVG ... N-terminal sequence, this fragment may represent a more highly glycosylated human equivalent of the $F_{342}$ ... $E_{373}$ fragment obtained from pig laryngeal aggrecan (FIGS. 3A and 3B to 5A–5C, fragment 5). Human aggrecan from adult articular cartilage is known to contain significantly more keratan sulphate than aggrecan from young pig laryngeal cartilage (26), and this could explain both the increased size and heterogeneity of the small human fragment (FIG. 9), compared with the pig fragment (35 kDa, FIGS. 4 and 5).

EXAMPLE 6

Figure 10:
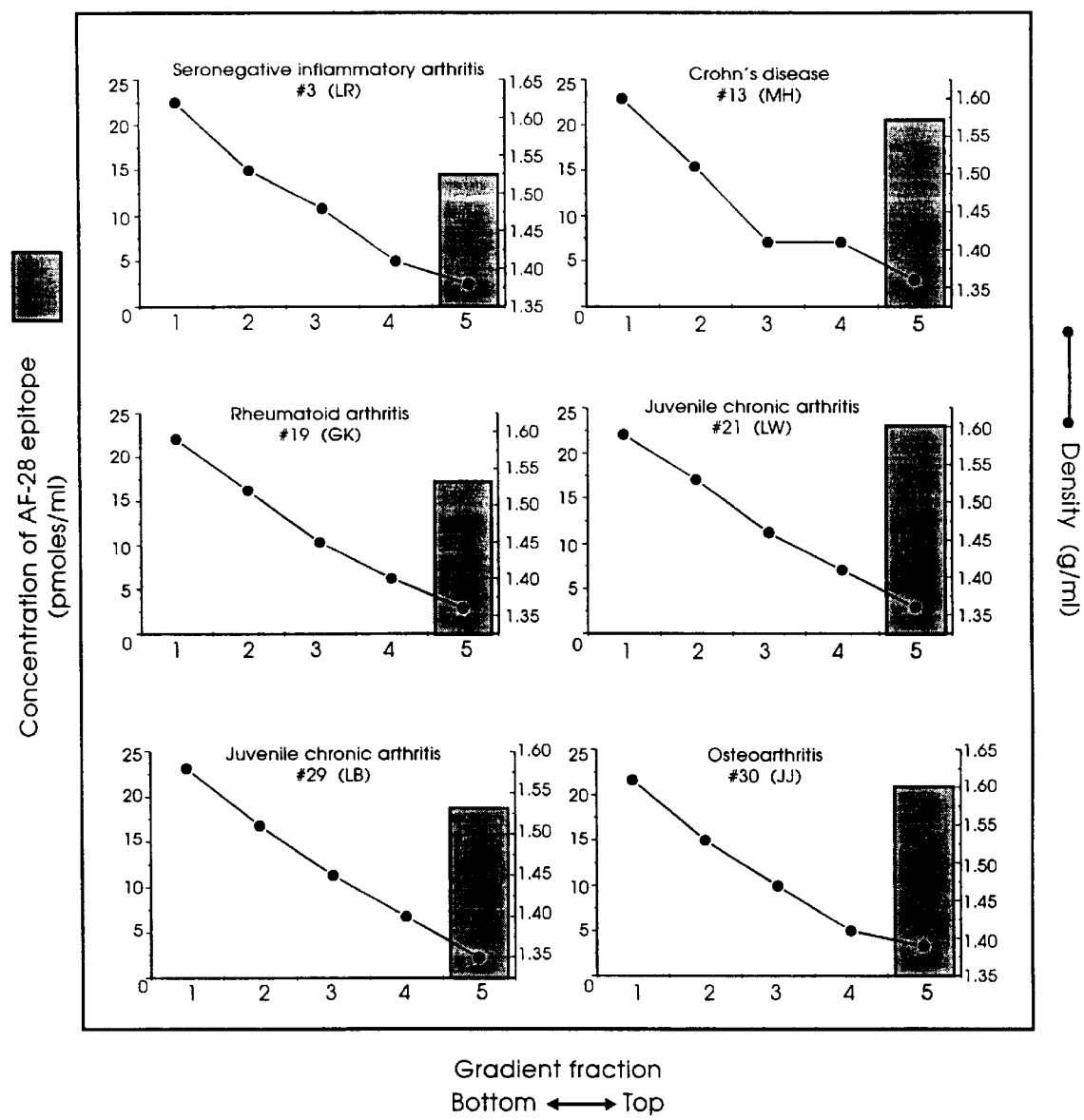
FIG. 10 shows the concentration of AF-28 epitope in synovial fluid from patients with different arthropathies, fractionated by caesium chloride density gradients.

Identification in Human Synovial Fluids of Low-Buoyant Density Aggrecan Fragments With FFGVG ... N-Termini Because of its small size, the 40,000–60,000 product with an FFGVG ... N-terminus is unlikely to have been detected in previous studies that have isolated large, high density aggrecan fragments with ARGSV ... N-termini (10,11). Large, high buoyant density aggrecan fragments are routinely recovered at the bottom (D1) of CsCl density gradients (δ>1.5), and ARGSVI-containing fragments have also been recovered in D1 fractions (10,11). Human synovial fluids were fractionated on CsCl density gradients to investigate the distribution of FFGVG-containing aggrecan fragments. Synovial fluids from patients with different arthropathies were diluted 1:2 with 8M guanidine-HCL and brought to 1.5 g/ml CsCl by the addition of solid CsCl. The samples were centrifuged for 16 hours at 10° C. at 34,000 rpm in a vertical rotor. The tubes were fractionated into 5 equal portions, with the D1 fraction at the bottom of the tube and the D5 fraction at the top. The density of each fraction was measured (FIG. 10), before exhaustive dialysis, freeze drying and reconstitution in one sixth the volume of distilled water, for determination of AF-28 epitope by competition ELISA (FIG. 10).

The results show that for all patient samples, aggrecan fragments containing FFGVG ... N-termini were recovered at the top of CsCl density gradients in the D5 fractions. No AF-28 epitope could be measured in the D1, D2, D3 or D4 fractions, suggesting that none of the fragments with FFGVG ... N-termini are large or of high buoyant density, and further suggesting that these fragments do not contain any chondroitin sulphate chains. These findings are compatible with a model which proposes that during catabolic processing, aggrecan is cleaved not only at the major MMP site, but also at the aggrecanase site. Based on the size of the larger AF-28 positive fragments ($M_r$ 150–200 kDa) identified by Western analysis of human synovial fluids (FIGS. 9A and 9B), there is probably also cleavage at a site located C-terminal to the G2 globular domain, but N-terminal to the chondroitin-sulphate-rich region.

Figure 11:
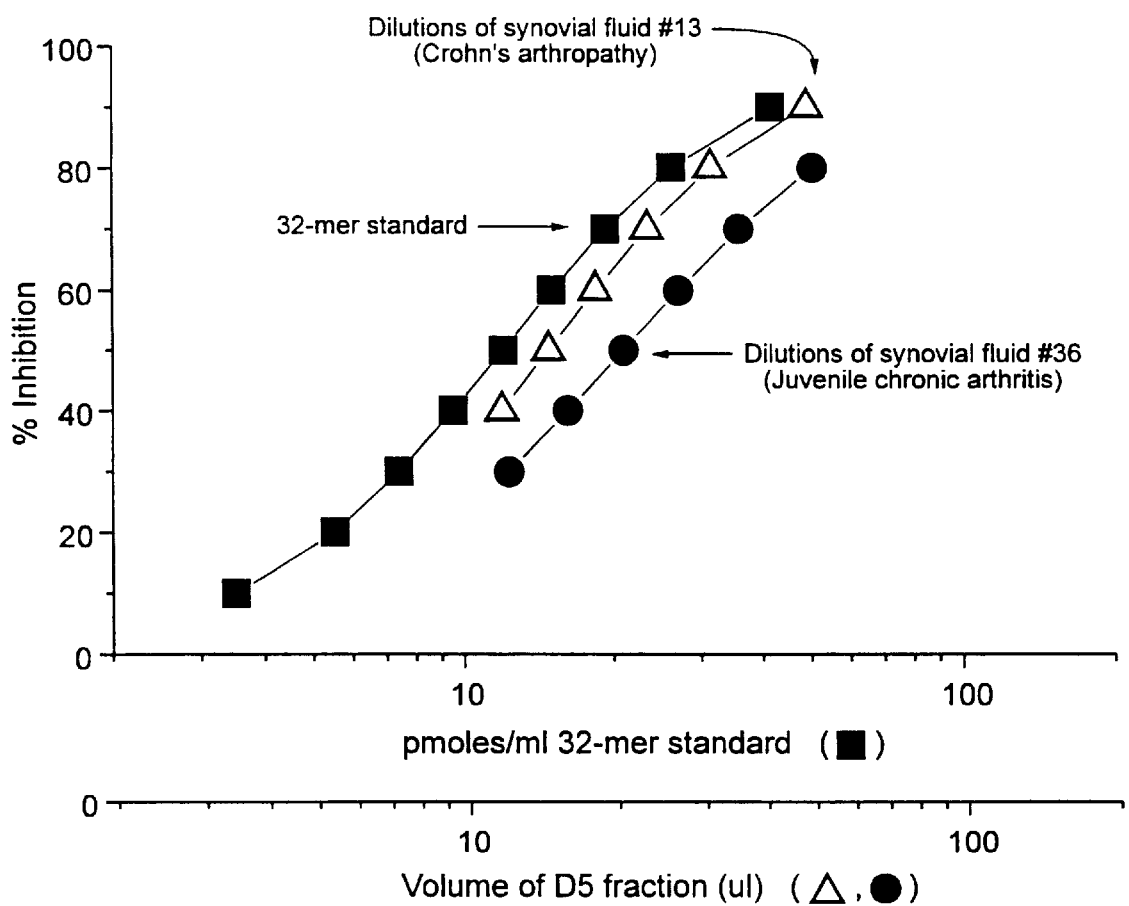
FIG. 11 shows the specificity of binding of AF-28 antibody to epitopes in the D5 fraction of synovial fluids after caesium chloride density gradient fractionation.

To eliminate the possibility that AF-28 was binding non-specifically to another component in the protein-rich D5 fraction of the CsCl density gradients, dilutions of D5 fractions were assayed by competition ELISA. AF-28 antibody binding specifically to dilutions of FFGVG ... neo-epitope would be expected to generate a competition curve with a slope parallel with the standard antigen. Non-specific binding, due to a weak and variable affinity of the antibody for the non-specific "antigen" would be expected to generate a non-parallel competition curve, or no curve at all. The inhibition curves presented in FIG. 11 show that the AF-28 epitope detected in the D5 fractions of CsCl density gradients represents AF-28 antibody binding specifically to aggrecan fragments with N-terminal FFGVG ... sequences.

This result indicates that AF-28 antibody is useful for the diagnosis and monitoring of treatment or disease progression in patients with active joint destruction and other conditions involving proteoglycan breakdown.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

Publications referred to herein are listed on the following pages, and are incorporated herein by this reference.

References

1. Fosang, A. J. & Hardingham, T. E. Biochem J, 1989 261 801–809
2. Fosang, A. J., Neame, P. J., Hardingham, T. E., Murphy, G. & Hamilton, J. A. J Biol Chem, 1991 266 15579–15582
3. Fosang, A. J., Neame, P. J., Last, K., Hardingham, T. E., Murphy, G. & Hamilton, J. A. J Biol Chem, 1992 267 19470–19474
4. Fosang, A. J., Last, K., Knäuper, V., Neame, P. J., Murphy, G., Hardingham, T. E., Tschesche, H. & Hamilton, J. A. Biochem J, 1993 295 273–276
5. Fosang, A.J., Last, K., Neame, P. J., Hardingham, T. E., Murphy, G., Hamilton, J. A. Orthopaed. Trans., 1993 17 848–849
6. Doege, K. J., Sasaki, M., Kimura, T. & Yamada, Y. J. Biol Chem, 1991 266 894–902
7. Ilic, M. Z., Handley, C. J., Robinson, H. C. & Mok, M. T. Archiv. Biochem. Biophys, 1992 294 115–122
8. Sandy, J. D., Neame, P. J., Boynton, R. E. & Flannery, C. R. J Biol Chem, 1991 266 8683–8685
9. Loulakis, P., Shrikhande, A., Davis, G. & Maniglia, C. A. Biochem J, 1992 284 589–593
10. Lohmander, L. S., Neame, P. J. & Sandy, J. D. Arthritis Rheum, 1993 36 1214–1222
11. Sandy, J. D., Flannery, C. R., Neame, P. J. & Lohmander, L. S. J Clin Invest, 1992 89 1512–1516
12. Mok, M. T., Ilic, M. Z., Handley, C. J. & Robinson, H. C. Archiv. Biochem. Biophys, 1992 292 442–447
13. Flannery, C. R., Lark, M. W. & Sandy, J. D. J. Biol. Chem., 1992 267 1008 1014
14. Bayne, E. K., Donatelli, S. A., Singer, I. I., Weidner, J. R., Hutchinson, N. I., Hoerrner, L. A., Williams, H. R., Mumford, R. A., Lohmander, L. S. & Lark, M. W. 40th Trans. Orthop. Res. Soc,1994 308

15. Fosang, A. J., Last, K., Neame, P. J., Hughes, C. E., Caterson, B., Hardingham, T. E., Knäuper, V., Murphy, G. & Tschesche, H. 40th Trans. Orthop. Res. Soc., (1994) 48
16. Fosang, A. J., Last, K., Neame, P. J., Murphy, G., Knäuper, V., Tschesche, H., Hughes, C. E., Caterson, B. & Hardingham, T. E. Biochem. J., 1994 304 347–351
17. Hughes, C. E., Caterson, B., Fosang, A. J., Roughley, P. J & Mort, J. S. 40th Trans. Orthop. Res. Soc., 1994 311 —and—Biochem. J., 1995 305 799–804
18. Lark et al. 40th Trans. Orthop. Res. Soc., 1994 313
19. Moore et al. 40th Trans. Orthop. Res. Soc., 1994 312
20. Di Pasquale, G., Caccese, R., Pasternak, R., Conaty, J., Hubbs, S. & Perny, K. Proc. Soc. Exp. Biol. Med., 1986 183, 262–267
21. Mort, J. S., Dodge, G., Roughley, P. J., Liu, J., Finch, S. J., Di Pasquale, G. & Poole, A. R. Matrix, 1993 13, 95–102
22. Fosang, A. J., Dudhia, J., Last, K., Royston, K. & Hamilton, J. A. 39th Trans. Orthop. Res. Soc., 1993 313
23. Fairbanks, G., Steck, T. L. & Wallach, D. F. H. Biochem, 1971 10 2606–2616
24. Carney, S. L., Bayliss, M. T., Collier, J. M. & Muir, H. Anal Biochem, 1986 156 38–44
25. Caterson, B., Calabro, T., Donohue, P. J. & Jahnke, M. R. Articular Cartilage Biochemistry, Eds. K. Kuettner et al, Raven Press, New York 1986, pp 59–73
26. Hardingham, T. E. & Bayliss, M. T. Semin. Arth. Rheu., 1991 1 12–33
27. Fosang, A. J., Last, K., Neame, P. J., Knaüper, V. & Murphy G. (1995) Collagenase-3 cleavage sites in the aggrecan interglobular domain. (manuscript in preparation)
28. Lark, M. W., Williams, H., Hoernner, L. A., Weidner, J., Ayala, J. M., Harper, C. F., Christen, A., Olszewski, J., Konteatis, Z., Webber, R. & Mumford, R. A. Biochem. J., 1995 307 245–252
29. Köhler G. and Milstein, C. Nature, 1975 256 495–497

I claim:

1. An antibody which specifically recognizes the amino acid sequence FFGVG (SEQ ID NO 5),
    said peptide being the N-terminal sequence of the carboxy-terminal sequence generated by proteolytic cleavage of aggrecan at the site N341-F342, and
    said antibody having the following characteristics:
    a) elicited by immunization with the peptide FFGV-GEEDC (SEQ ID NO 8);
    b) having the ability to detect cleavage fragments generated by matrix metalloproteinases, but not those generated by cathepsin B, elastin or trypsin; and
    c) having the ability to detect three fragments generated by matrix metalloproteinase-8;
    wherein the antibody is monoclonal antibody AF-28 which is produced by the hybridoma cell line designated ATCC HB11671.

2. An antibody according to claim 1, wherein the antibody recognizes the peptide sequence FFGVGGE-EDITVQTVTWPDMELPLPRNITEGE (FFGVGG . . . EGE 32-mer): SEQ ID NO 4.

3. A hybridoma cell line according to claim 1, designated ATCC HB11671.

4. A method of detecting an aggrecan degradation product in a sample, comprising the steps of:
    (1) reacting said sample with an antibody according to claim 1; and
    (2) detecting bound antibody with an antiserum, wherein said antiserum is directed against an immunoglobulin labelled with a detectable marker.

5. A method according to claim 4, wherein the sample is a biological sample.

6. A method according to claim 5, wherein the sample is a mammalian body fluid.

7. A method according to claim 6, wherein the mammalian body fluid is selected from the group consisting of blood, serum, synovial fluid, lymph and urine.

8. A method according to claim 4, wherein the sample is of human origin.

9. A method according to claim 4, wherein the sample is selected from the group consisting of cell culture media, tissue culture media, tissue extracts, and cell extracts.

10. A method according to claim 4, which is a competition ELISA assay.

11. A method according to claim 10 which is a competition assay in which the competing peptide comprises the N-terminal sequence comprising a sequence of FFGVG.

12. A method according to claim 10, which is a competition assay in which the competing peptide is FFGVGG (SEQ ID No. 3).

13. A method according to claim 10 in which the competing peptide is FFGVGGEEDITVQTVTWPDMELPLPRNITEGE (FFGVGG . . . EGE 32-mer) (SEQ ID NO. 4).

14. A method according to claim 4, which is a sandwich ELISA assay.

15. A method according to claim 14 which is a sandwich assay in which an anti-keratan sulphate antibody or an anti-aggrecan antibody is used as a capture antibody to bind aggrecan fragments.

16. A method according to claim 15 in which the anti-keratan sulphate antibody is monoclonal antibody 5-D-4.

17. A method according to claim 4, which utilizes an assay standard selected from the group consisting of recombinant aggrecan interglobular domain, purified aggrecan interglobular domain, MMP-treated recombinant aggrecan core protein, and MMP-treated purified aggrecan core protein.

* * * * *

```
                        SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
          (A) LENGTH: 7 amino
acids
          (B) TYPE: amino acid
          (C) STRANDEDNESS: Not R
elevant
          (D) TOPOLOGY: Not Relev
ant (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ
ID NO:1:

Phe Val Asp Ile Pro Glu Asn
     1
  5

(2) INFORMATION FOR SEQ ID NO:2:

(i) SEQUENCE CHARACTERISTICS:
          (A) LENGTH: 6 amino
acids
          (B) TYPE: amino acid
          (C) STRANDEDNESS: Not R
elevant
          (D) TOPOLOGY: Not Relev
ant (ii) MOLECULE TYPE: peptide (iii) HYPOTHETICAL: NO (iv) ANTI-SENSE: NO (v) FRAGMENT TYPE: C-terminal
```

(xi) SEQUENCE DESCRIPTION: SEQ
ID NO:2:

Val Asp Ile Pro Glu Asn
    1
 5

(2) INFORMATION FOR SEQ ID NO:3:

(i) SEQUENCE CHARACTERISTICS:
        (A) LENGTH: 6 amino
acids
        (B) TYPE: amino acid
        (C) STRANDEDNESS: Not R
elevant
        (D) TOPOLOGY: Not Relev
ant (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ
ID NO:3:

Phe Phe Gly Val Gly Gly
    1
 5

(2) INFORMATION FOR SEQ ID NO:4:

(i) SEQUENCE CHARACTERISTICS:
        (A) LENGTH: 32 amino
acids
        (B) TYPE: amino acid
        (C) STRANDEDNESS: Not R
elevant
        (D) TOPOLOGY: Not Relev
ant (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ
ID NO:4:

Phe Phe Gly Val Gly Gly Glu Glu
Asp Ile Thr Val Gln Thr Val Thr
    1
 5
 10
 15

Trp Pro Asp Met Glu Leu Pro Leu
Pro Arg Asn Ile Thr Glu Gly Glu
                20
                25
                30

(2) INFORMATION FOR SEQ ID NO:5:

(i) SEQUENCE CHARACTERISTICS:
        (A) LENGTH: 5 amino
acids
        (B) TYPE: amino acid
        (C) STRANDEDNESS: Not R
elevant
        (D) TOPOLOGY: Not Relev (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:5:

Phe Phe Gly Val Gly
     1               5

(2) INFORMATION FOR SEQ ID NO:6:

(i) SEQUENCE CHARACTERISTICS:
             (A) LENGTH: 9 amino acids
             (B) TYPE: amino acid
             (C) STRANDEDNESS: Not Relevant
             (D) TOPOLOGY: Not Relevant (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:6:

Phe Gly Val Gly Gly Glu Glu Asp Ile
     1               5

(2) INFORMATION FOR SEQ ID NO:7:

(i) SEQUENCE CHARACTERISTICS:
             (A) LENGTH: 10 amino acids
             (B) TYPE: amino acid
             (C) STRANDEDNESS: Not Relevant
             (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:7:

Asp Ile Pro Glu Asn Phe Phe Gly Val Gly
     1               5                   10

(2) INFORMATION FOR SEQ ID NO:8:

(i) SEQUENCE CHARACTERISTICS:
             (A) LENGTH: 9 amino acids

```
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:8:

Phe Phe Gly Val Gly Glu Glu Asp Cys
    1               5

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:9:

Asp Ile Pro Glu Asn Phe Phe Gly
    1               5
```